United States Patent [19]
Jamieson et al.

[11] 4,387,598
[45] Jun. 14, 1983

[54] PIPE SCANNER MECHANISM

[75] Inventors: John M. Jamieson, Herndon; Dixon Cleveland, Annandale, both of Va.

[73] Assignee: Electric Power Research Institute, Palo Alto, Calif.

[21] Appl. No.: 302,459

[22] Filed: Sep. 15, 1981

[51] Int. Cl.³ .............................................. G01N 29/04
[52] U.S. Cl. ........................................ 73/637; 73/622; 73/640
[58] Field of Search ................ 73/637, 622, 638, 640; 250/358.1; 324/221

[56] References Cited
U.S. PATENT DOCUMENTS

| 3,445,655 | 5/1969 | Curry ............................. | 250/358.1 |
| 4,331,034 | 5/1982 | Takeda et al. ..................... | 73/637 |

FOREIGN PATENT DOCUMENTS 52-33584  3/1977  Japan ................................... 73/637

*Primary Examiner*—Howard A. Birmiel

[57] ABSTRACT

A device for the total circumferential scanning of pipes and pipe joints is provided comprising a housing accommodating a tooth drive roller, drive means connected to said toothed drive roller, toothed idler rollers, a plurality of smooth idler rollers, scanning means for detecting faults and imperfections in pipes and pipe joints, and a flexible belt toothed on one surface thereof having a length greater than the circumference of the pipe to be scanned and having ends adapted to be securely joined together, said belt being adapted to be routed circumferentially around said pipe and through said housing by contacting each of said rollers whereby said belt is automatically aligned around said pipe so that said device circumferentially traverses the pipe in a plane perpendicular to the pipe axis.

2 Claims, 2 Drawing Figures

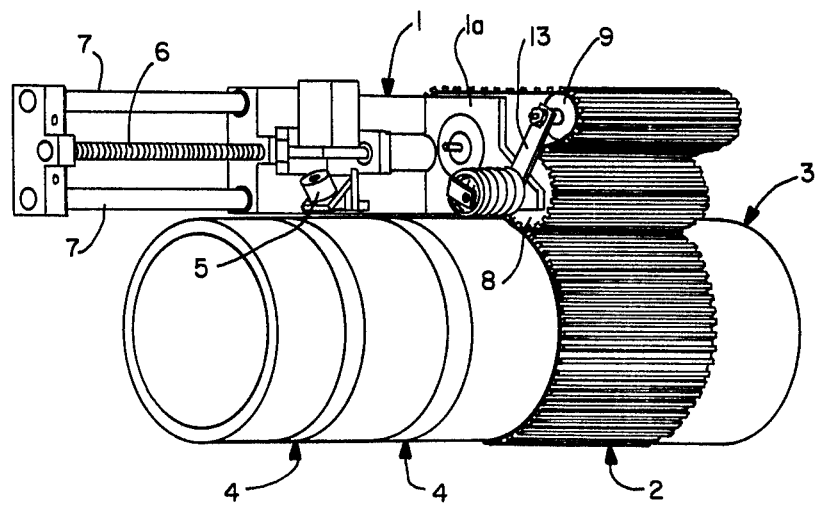
FIG.—1
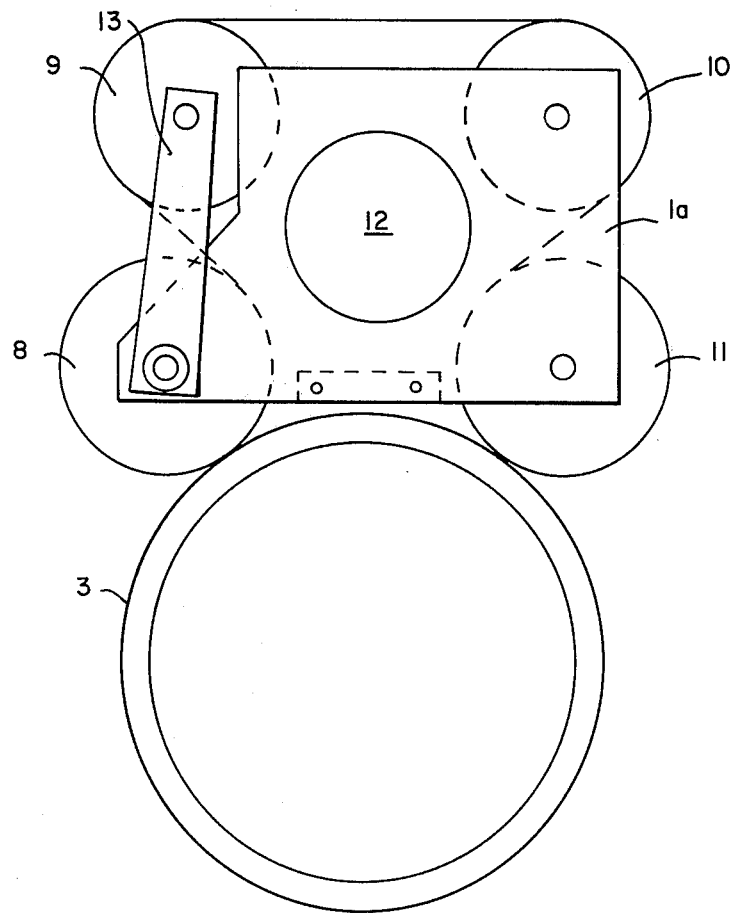
FIG.—2

PIPE SCANNER MECHANISM

BACKGROUND OF THE INVENTION

The present invention is drawn to a device for circumferentially traversing a pipe of substantial diameter wherein such a device is useful for accommodating a scanning instrument, such as an ultrasonic instrument, photographic instrument or other instrument which may be used to detect faults, cracks or other imperfections which may occur in pipe welds or other pipe joints and in pipe casings. Such pipes of substantial diameter may be found in pipelines, ships, refineries or other industrial installations for use in transporting gases, petroleum products, steam, liquid chemicals, etc. In order to properly maintain such pipes, it is desirable to have a device which may circumferentially scan the welds and joints of any section of the pipe and it is further desirable to have such device adaptable for rapid attachment and detachment from the pipe.

Such devices heretofore known in the prior art are of two types. One type is a sector scanner which may run on a machined rubber track. However, such prior art device suffers from the disadvantage of having to be remounted after each sector is traversed in order to complete circumferential scanning of the pipe. Such a device must also be realigned with each adjustment in order to maintain true circumferential line around the section of pipe to be scanned. The second type of device requires the attachment of a rigid, circular track around the pipe to be scanned. While this may allow 360° of scanning around a true circumferential line, the constant need to attach and detach the rigid track along each section of pipe may be inconvenient. Furthermore, because the track is rigid there is a need to carry various sizes of circular tracks to accommodate various diameters of pipes. The device according to the instant invention does not suffer from the aforementioned disadvantages of the devices known in the prior art.

DESCRIPTION OF THE INVENTION

FIG. 1 is a perspective view of a device according to the instant invention shown mounted on a section of pipe.

FIG. 2 is a schematic of an end view of a device according to the instant invention mounted on a section of pipe.

It is an object of the present invention to provide a pipe scanner which may be rapidly attached and detached to a section of pipe to be scanned be a flexible belt.

It is a further object of the instant invention to provide a pipe scanner which may circumferentially scan a section of pipe along a track of flexible belt wherein manual centering of the scanner and the flexible belt on the pipe is not required. It is a further object to facilitate the axial alignment of the device with the pipe by providing a flexible belt of substantial width and by providing a means on the device for tensioning the belt around the pipe and through the scanning device, thereby causing the scanner to track on the shortest circumferential path around the pipe, i.e., on a plane perpendicular to the pipe axis.

Referring to FIG. 1, the scanning device 1 according to the instant invention is shown attached by the tensioned tracking belt 2 onto pipe 3. The device is aligned so as to scan pipe welds or joints 4 by way of scanning instrument 5 which is accommodated by device 1. Once the belt 2 has been fixed onto the pipe, driving means within the housing of the device may propel the device to circumferentially scan the pipe. The scanning instrument 5 may be axially adjusted along the length of the pipe by motor or by hand by movement along support members 7 and axial drive screws 6.

Referring to FIG. 2, it is shown that four rollers 8, 9, 10 and 11 and drive motor 12 are accommodated by housing 1a of the device 1. Rollers 8 and 11 are toothed (non shown) in order to mesh with the toothed belt 2 (not shown in FIG. 2). Rollers 9 and 10 have smooth surfaces. Roller 9 is connected to spring-loaded idler arms 13 which are adapted to pivot on housing 1a to adjust the tension on belt 2. Drive motor 12 and reducing gears (not shown) are located within the housing of 1a and are engaged to one of the rollers 8 or 11 in order to drive the scanner around the pipe. Preferentially roller 11 is driven by the motor 12. The belt 2 which is toothed on one surface thereof is routed around the pipe 3 with the smooth side of said belt against the pipe. For the purposes of definition, the following routing of the belt through the rollers will be described with the rollers in a stationary position. The surface of each roller which faces towards the drive motor 12 will be described as the interior surface of the roller and the surface of each roller which faces away from the drive motor 12 will be described as the exterior surface of the roller. Belt 2 is therefore routed with its toothed surface meshed with the interior surface of toothed roller 8, and further routed with its smooth surface in contact with the exterior surfaces of roller 9 and 10, and finally with its toothed surface meshed with the interior surface of roller 11. The ends of belt 2 are attached to each other by means which will ensure secure attachment but which will not interfere with the routing of the belt around the respective rollers and the pipe. Preferably the ends of the belt 2 are attached with commercially available alligator lacing. The scanning device 1 therefore moves around the pipe 3 by feeding the belt 2 onto roller 8 and off roller 11, or onto roller 11 and off roller 8, as the drive roller 11 is driven counterclockwise or clockwise, respectively.

Centering of the belt 2 is not needed on the pipe since the device 1 and belt 2 ride directly on the pipe and axial alignment automatically occurs due to the substantial width of the belt and the tension thereon caused by stretching of the belt and by spring-loaded idler arms 13.

Although we have described particular embodiments of our invention above, it is intended that the invention not be limited thereby except by the scope of the following claims.

What is claimed is:

1. A device for total circumferential scanning of pipes and pipe joints comprising a housing accommodating a toothed drive roller, driving means connected to said toothed drive roller, a toothed idler roller and a plurality of smooth idler rollers, wherein at least one of said smooth idler rollers is connected to said housing by pivoting arms adapted for tensioning by spring means, and scanning means for detecting faults and imperfections in said pipes and pipe joints; said device further comprising a flexible belt toothed on one surface thereof and having a length greater than the circumference of the pipe to be scanned and having ends adapted to be securely joined together, said belt adapted to be routed circumferentially around said pipe and through said housing by contacting each of said rollers whereby the toothed surface of said belt contacts said toothed drive roller and toothed idler roller and the smooth surface of said belt contacts said pipe and said smooth idler rollers.

2. A device according to claim 1 wherein said rollers and said belt are of substantial width such that when said device is mounted on said pipe and said belt is tensioned by said pivoting arms adapted for tensioning, said belt is automatically aligned around said pipe so that said device circumferentially traverses said pipe in a plane perpendicular to the pipe axis.

* * * * *